United States Patent [19]

Iwatschenko

[11] Patent Number: 4,898,581
[45] Date of Patent: Feb. 6, 1990

[54] DEVICE FOR ADMINISTERING LIQUID

[75] Inventor: Peter Iwatschenko, Neunkirchen, Fed. Rep. of Germany

[73] Assignee: Pfrimmer-Viggo GmbH & Co. KG, Erlangen, Fed. Rep. of Germany

[21] Appl. No.: 364,546

[22] Filed: Jun. 5, 1989

Related U.S. Application Data

[63] Continuation of Ser. No. 157,917, Feb. 19, 1988, abandoned.

[30] Foreign Application Priority Data

Feb. 19, 1987 [DE] Fed. Rep. of Germany ....... 3705357
Oct. 29, 1987 [EP] European Pat. Off. ........... 87115896

[51] Int. Cl.$^4$ .......................... A61M 5/00; E16K 5/14
[52] U.S. Cl. ................................... 604/122; 604/247; 137/854
[58] Field of Search ................ 604/122, 247; 137/843, 137/854, 853

[56] References Cited

U.S. PATENT DOCUMENTS 4,223,813  9/1980  Garrett et al. .
4,232,677 11/1980  Leibinsohn ........................... 604/247
4,487,604 12/1984  Iwatschenko et al. .
4,550,749 11/1985  Krikorian ............................ 137/854
4,615,693 10/1986  Paradis et al. ...................... 604/122
4,684,366  8/1987  Sawyer et al. ................... 604/247 X

FOREIGN PATENT DOCUMENTS 0182045 5/1986 European Pat. Off. .
3035748 5/1982 Fed. Rep. of Germany .
3217028 5/1983 Fed. Rep. of Germany .
3138267 4/1985 Fed. Rep. of Germany .

Primary Examiner—Stephen C. Pellegrino
Attorney, Agent, or Firm—Brumbaugh, Graves, Donohue & Raymond

[57] ABSTRACT

A device for administering liquid in a device for the parenteral administration of liquid, comprising a pump which conveys the liquid through an elastic tube to the patient, the entry of air into the tube is prevented by the provision of a valve (20) in the tube downstream of the pump. This valve opens in the patient's direction under a pressure of such magnitude that the pressure inside the tube upstream of the valve is at least approximately as great as the external air pressure. The check valve provided may be used together with a pump as well as under mere gravity feeding.

8 Claims, 3 Drawing Sheets

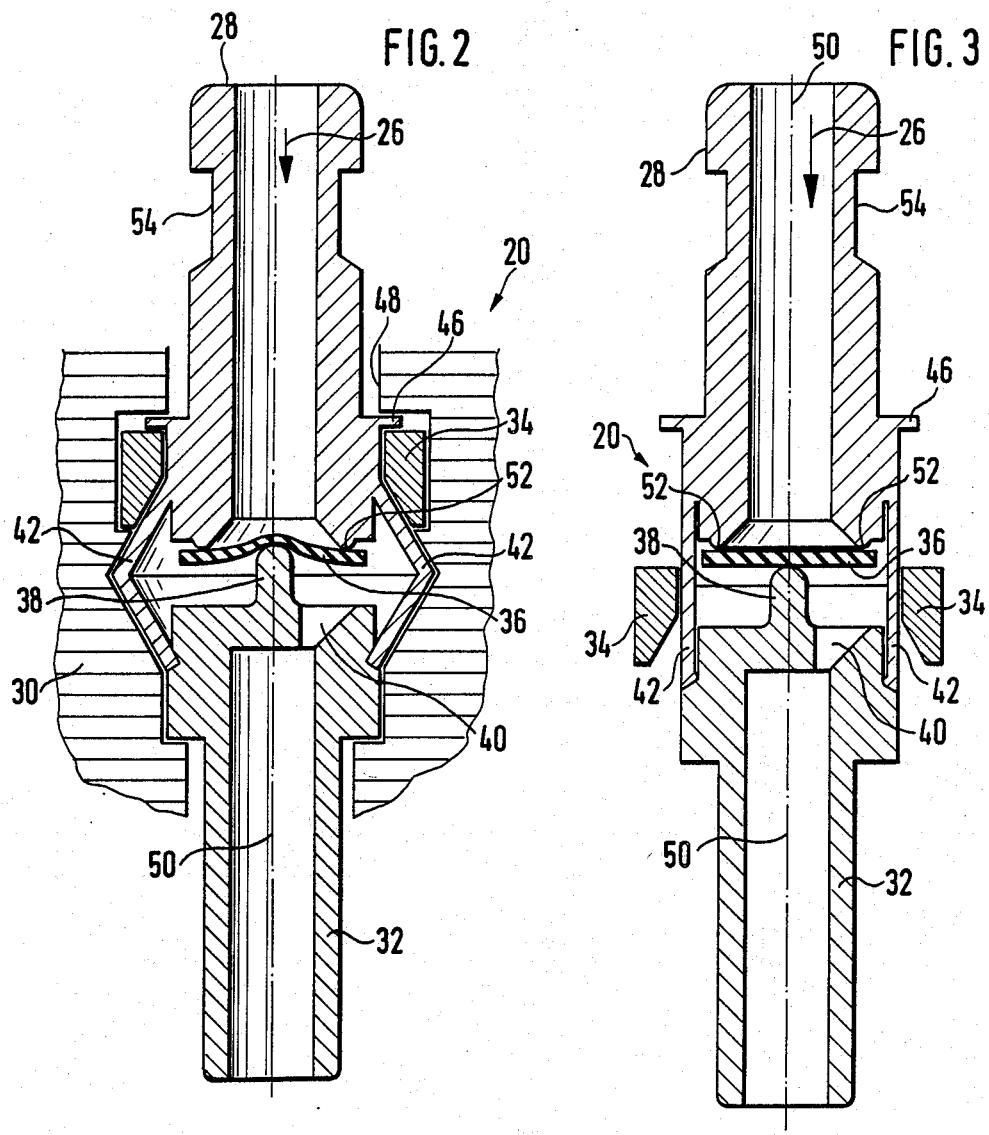

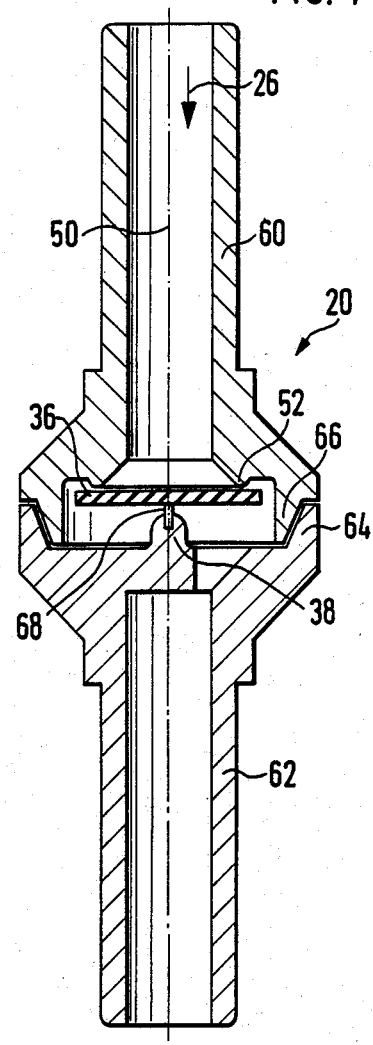
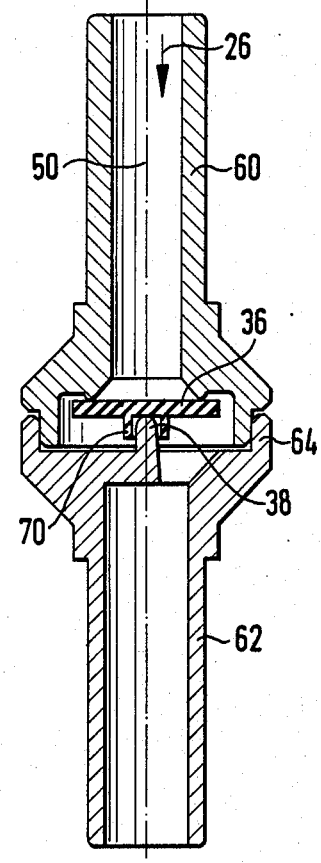
FIG. 4
FIG. 5

DEVICE FOR ADMINISTERING LIQUID

This application is a continuation of application Ser. No. 157,917, filed on Feb. 19, 1988.

This invention relates to a device for parenteral administration of liquid as well as a check valve for use in such device.

When a patient is fed parenterally, the nutrients are supplied directly into a vein, bypassing the gastrointestinal tract. Apart from nutrients, also drugs may be introduced continuously in this manner into the circulation.

Devices for parenteral administration of liquids usually comprise a supply bottle for the liquid which is metered out of the same, passing through an elastic tube to a syringe which terminates directly in a vein. The liquid is conveyed through the tube by way of a pump and/or gravity of the liquid.

Protection of the patient requires that devices for the parenteral administration of liquids meet high safety demands. In particular, it must be warranted at all costs that the feed rate, in other words the amount of liquid which the patient is given per unit time and which usually is indicated as the volume per unit of time or drops per unit of time, does not exceed a predetermined limit value. Any excess quantity administered beyond the limit value might be lethal. Besides, air must not enter the patient's vein under any circumstances.

Conventional devices for parenteral administration of liquids thus involve great expenditure for safety measures. Such safety means in the first place relate to the so-called "first errors". A "first error" is understood to be the failure of a protective or monitoring system possibly leading to an immediate risk of the patient's safety.

If air gets into the supply tube, the device must interrupt the feeding of liquid into the vein within a span of time which is shorter than the time period which it takes for the air to reach the syringe. The period of time from the instant at which an error occurs, such as the entry of air into the tube up to the moment at which a safe condition is established, for instance when the output is terminated is called "error reaction time". This error reaction time under any circumstances must be so short that danger to the patient is avoided if an error does happen.

Air sensors are known in the art to avoid the delivery of air. They give alarm as soon as air is present in the tube leading to the patient. Ultrasonic means and light barriers are known for use as air sensors. These devices are rather expensive and, moreover, they have the disadvantage of merely providing a "diagnosis" rather than positively preventing the entry of air. Consequently they do not improve the availability of the device.

The problem of air entering the tube is particularly acute if a feed pump is employed in the supply tube. Such pumps are known for example from DE-PS 31 38 267. They work with silicone tubes, and silicone is permeable to air so that gases may penetrate into the interior of the tube if the pressure inside the tube is less than the pressure of the ambient air (atmosphere). This would have the fatal consequences already mentioned.

In the case of known devices for parenteral administration of liquids, low pressure in the silicone tube acted on by the feed pump may have two causes: On the one hand, if there is an occlusion of the tube in the range of the pump, the liquid column "pending" in downward direction toward the patient may cause low pressure, particularly in the upper section of the tube just below the occluded location. On the other hand, certain operating phases of the pump which need not be dealt with in detail here may involve brief periodic low pressure in the silicone tube downstream of the pump.

It is the object of the invention to provide a device for parenteral administration of liquid, comprising a pump which conveys the liquid through an elastic tube to the patient, with which device it is guaranteed that air will not enter into the tube.

This object is met, in accordance with the invention, in that a valve is disposed in the tube downstream of the pump which valve opens in the direction toward the patient under a pressure of such magnitude that the pressure inside the tube upstream of the valve is at least approximately as great as the external air pressure.

With the device according to the invention consequently it cannot happen that the pressure inside the tube is lower than the nitrogen partial pressure of the atmosphere surrounding the tube because a "pending liquid column" causes suction or because there are certain operating phases of the pump during which the pump briefly sucks contrary to the feeding direction. Any penetration of gases into the tube thus is positively excluded as sufficiently high pressures always prevails in the silicone tube segment up to the valve.

The so-called "free flow" (unobstructed passage of the liquid through the tube into the vein) likewise is prevented by the valve according to the invention.

In a preferred modification of the invention it is provided that at least two different opening pressures are adjustable at the valve. In this case the higher opening pressure is effective if the valve is utilized together with a feed pump with which the valve is positively coupled mechanically in corresponding manner. Such a check valve according to the invention thus fulfills two different functions: If the valve is employed together with a pump, the assembly of valve and pump automatically causes the higher opening pressure of the valve to be set because of a positive mechanical coupling of the joined members. On the other hand, such a valve likewise may be used without a pump. In that event the lower opening pressure is set automatically so that alternately the valve is useful also in a gravity feeding device (i.e. without pump).

Regardless of the use described above in the parenteral administration of liquids, the valve provided by the invention is useful for other medical purposes as well, and it is characterized by having a simple structure and therefore being producible at low cost while offering high operating reliability. The valve permits adjustment of extremely low opening pressures.

True, a check valve with which the opening pressures can be very low is known from EP 0 182 045. However, in that case two pegs act on the elastic membrane at the side thereof which is remote from the valve seat. It is costly to manufacture a valve member provided with two pegs and, moreover, the valve structure according to EP 182 045 requires a dual layer membrane.

The check valve according to the invention with which a single peg acts at least approximately centrally on the membrane at the side thereof which is remote from the valve seat, is characterized in that dual point support is warranted in any operating condition (i.e. whether the valve is open or closed). Any radial displacement of the membrane thus is impossible. The membrane remains centered and cannot become engaged with the walls surrounding it radially, a condition which might lead to friction and impair the proper functioning.

The check valve according to the invention guarantees perfect functioning, both in opening and in closing senses even if the pressure differences are minute, in the range of a few centimeters of water column.

In a preferred modification of the check valve it is provided that the central peg is displaceable axially so that the bias of the membrane and consequently the opening pressure of the valve are variable.

It is likewise conceivable to provide a guide means between the peg and the membrane, for instance in the form of an axial pin on the membrane for axial entering into a recess formed in the peg, thereby positively excluding any slipping of the membrane in radial direction.

Embodiments of the invention will be described in greater detail below, with reference to the drawing, in which:

FIG. 2 shows a check valve used with a device according to FIG. 1 and coupled to a pump;

FIG. 3 shows a valve according to FIG. 2 being used without a pump;

FIG. 4 shows another embodiment of a check valve; and

FIG. 5 shows a special modification of a check valve.

Figure 1:
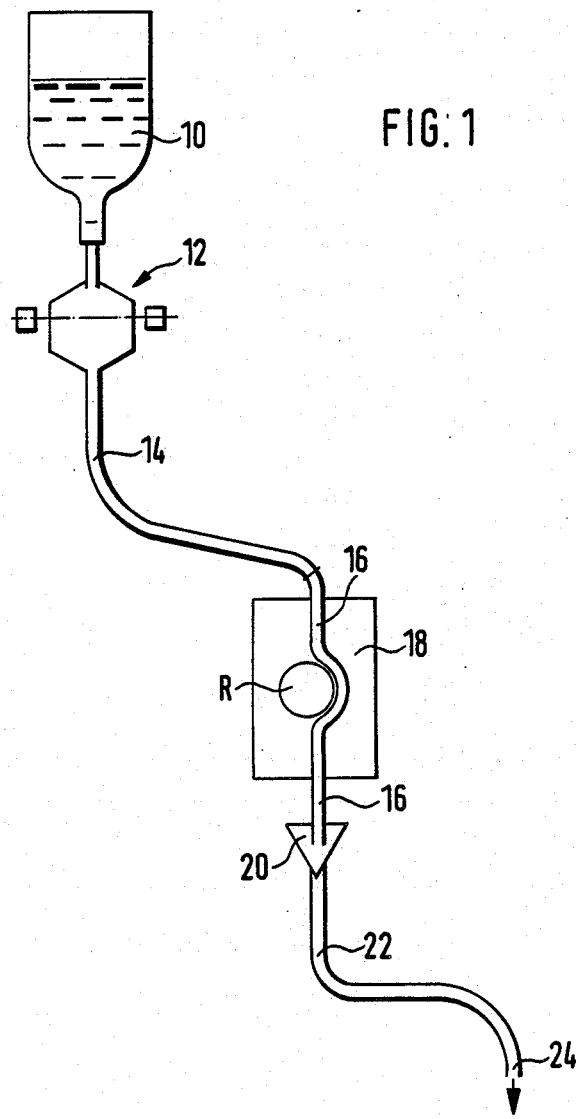
FIG. 1 is a diagrammatic presentation of a device for parenteral administration of liquid.

FIG. 1 shows a bottle 10 containing a liquid to be administered, such as a nutrient or medicine. A drop sensor 12 of conventional structure monitors the feed rate. The liquid is guided towards the pump 18 substantially in vertical downward direction, i.e. the direction of gravity by means of an elastic tube 14 made of polyvinylchloride (PVC). In contrast to tube 14 the tube segment 16 passing through the pump 18 is made of silicone. Downstream of the pump 18 there is a check valve 20 which will be described in greater detail below. The check valve 20 is followed by another tube 22 which is made of PVC just like the tube 14 and which passes on to the patient (not shown) in the direction of arrow 24. Except for the valve 20, the device shown in FIG. 1 is of conventional kind.

FIG. 2 is a detailed presentation of the valve 20 used in a device according to FIG. 1. The direction of flow of the liquid through the valve 20 is indicated by arrow 26.

The silicone tube segment 16 (not shown in FIG. 2, cf. FIG. 1) is connected upstream of the tube segment connector 28.

In FIG. 2 reference numeral 30 and horizontal hatching indicate a member 30 of the pump 18. It is into this member 30 of the pump 18 that the valve 20 shown in FIG. 2 is slipped. The PVC tube marked by reference numeral 22 in FIG. 1 is connected to the valve 20 by means of a tube connector 32.

Details of the valve 20 may be gathered from FIGS. 2 and 3, FIG. 2 showing the valve as coupled mechanically to the pump member 30, while the valve is shown in FIG. 3 in a condition in which it can be used without a pump.

A slip ring 34 is axially displaceable and adopts an upper position in the state illustrated in FIG. 2. A peg 38 acts centrally on a silicone membrane 36 which presents the opening and closing member of the valve. The opening pressure of the valve 20 is determined by the elasticity of the membrane 36. When the pressure difference in the direction of arrow 26 at the membrane 36 exceeds the contact pressure of the membrane against valve seat 52, the membrane 36 deflects in downward direction from the closing position illustrated in FIG. 2, thereby opening a passage through channel 40 into the tube connector piece 32. In assembled state in the pump member 30, shown in FIG. 2, a bellows 42 of the valve 20 is needed because of adaptation in form lock to the pump member 30 in spread position in which the peg 38 is displaced axially toward the membrane 36, as compared to the state shown in FIG. 3. And the membrane presses with greater force against the valve seat 52 so that the opening pressure of the valve is greater in the state illustrated in FIG. 2 than it is in the condition according to FIG. 3.

Aside from the bellows 42 the slip ring 34, too, is fit in form lock into the pump member 30 so as to release the bellows 42 into spread position. At the top the slip ring 34 touches a flange 46 of the tube segment connector 28, the flange itself being clamped between the slip ring 34 and a stop 48 formed at the pump member 30.

A recess 54 is provided in the upper portion of the tube segment connector 28. The silicone tube segment 16, when pushed on, is adapted to be secured in this recess by a retaining ring.

When the valve 20 is in the position shown in FIG. 3 the slip ring 34 takes care that the bellows 42 remains in stretched position, whereby the peg 38 is pushed downwards in the direction of the valve axis 50 and the contact pressure of the membrane 36 against the valve seat 52 is reduced as compared to the position shown in FIG. 2.

When in the condition shown in FIG. 3, the valve 20 may be used without a pump in the parenteral administration of liquid which, in this case, is fed by its gravity alone.

FIG. 4 shows a check valve which is characterized by simple structure and great operating reliability. Members corresponding to those of the embodiment according to FIGS. 2 and 3 are marked by the same reference numerals. The check valve shown in FIG. 4 comprises an upper member 60 and a lower member 62. The upper member 60 is formed with the annular valve seat 52, while the peg 38 is formed on the lower member 62. The two members are joined in close fit by means of a flange 64 at the lower member 62 and a projection 66 at the upper member 60. In closing state and in opening state it is warranted that the membrane 36 is supported on two radially spaced points. Therefore, radial displacement of the membrane in the direction of the adjacent walls is prevented. In addition to this securing of the membrane, the embodiment shown in FIG. 4 includes a pin 68 which is provided on the membrane 36 to engage into a complementary recess in the peg 38, thus reliably centering the membrane 36.

The valve illustrated in FIG. 4 is suitable for medical applications in general, especially for the administration of liquids.

FIG. 5 shows another embodiment of a check valve with which the membrane 36 is provided with an annular projection 70 presenting a recess which is engaged by the peg 38 so as to secure the membrane in centered position.

What is claimed is:

1. A check valve for a device for parenteral administration of a liquid, which comprises:
a tube segment connector having an annular valve seat at one end and a central axis;

a tube connector piece adjacent to the tube segment connector, the tube connector piece having a central axis and a peg centrally located on one end, wherein the annular valve seat is located adjacent to the peg and the central axes of the tube connector piece and the tube segment connector are aligned to form a central axis of the check valve;

an elastic membrane suspended perpendicular to the central axis of the check valve between the annular valve seat and the peg and biased against the annular valve seat by the peg, the peg being displaceable along the central axis of the check valve by a bellows surrounding the annular valve seat; and a selectively positionable locking means for variably compressing the bellows and displacing he peg so as to adjust the bias of the membrane against the annular valve seat thereby adjusting the opening pressure of the check valve.

2. The check valve according to claim 1, wherein the elastic membrane is held in the center of the annular valve seat by a guide means attached to the peg.

3. The check valve according to claim 1, wherein the elastic membrane comprises silicon.

4. The check valve according to claim 1, wherein the elastic membrane is in the shape of a plate.

5. The check valve according to claim 1, wherein the elastic membrane is provided with a recess that is engaged by the peg.

6. The check valve according to claim 1, wherein the locking means comprises a slip ring disposed around the outside of the bellows.

7. The check valve according to claim 1 attached to an elastic tube for conveying liquid, such that the internal pressure of the elastic tube is equal to or greater than the external air pressure.

8. The check valve according to claim 7, wherein the elastic tube is connected to a pump, and the peg is locked in position along the central axis of the valve housing, such that the bias of the elastic membrane is increased against the annular valve seat.

* * * * *